United States Patent
Bresch et al.

(10) Patent No.: US 9,943,371 B2
(45) Date of Patent: Apr. 17, 2018

(54) SYSTEM FOR CAMERA-BASED VITAL SIGN MEASUREMENT

(71) Applicant: KONINKLIJKE PHILIPS N.V., Eindhoven (NL)

(72) Inventors: Erik Bresch, Eindhoven (NL); Jens Muehlsteff, Aachen (DE); Timo Tigges, Berlin (DE); Alexander Dubielczyk, Gaertringen (DE); Caifeng Shan, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 179 days.

(21) Appl. No.: 14/401,659

(22) PCT Filed: Jun. 11, 2013

(86) PCT No.: PCT/IB2013/054764
§ 371 (c)(1),
(2) Date: Nov. 17, 2014

(87) PCT Pub. No.: WO2013/186696
PCT Pub. Date: Dec. 19, 2013

(65) Prior Publication Data
US 2015/0105670 A1 Apr. 16, 2015

Related U.S. Application Data

(60) Provisional application No. 61/658,538, filed on Jun. 12, 2012, provisional application No. 61/739,770, filed on Dec. 20, 2012.

(51) Int. Cl.
*A61B 5/00* (2006.01)
*A61B 19/00* (2006.01)
(Continued)

(52) U.S. Cl.
CPC ............ *A61B 19/54* (2013.01); *A61B 5/0077* (2013.01); *A61B 5/02416* (2013.01);
(Continued)

(58) Field of Classification Search
CPC ..... A61B 5/1127; A61B 5/113; A61B 5/4818; A61B 6/463; A61B 6/541; A61B 5/08; A61B 5/055
See application file for complete search history.

(56) References Cited

U.S. PATENT DOCUMENTS

| 9,020,185 B2 * | 4/2015 | Mestha ................ A61B 5/0075 382/100 |
| 9,386,923 B2 | 7/2016 | Winter et al. |

(Continued)

FOREIGN PATENT DOCUMENTS

| EP | 2380493 A1 | 10/2011 |
| JP | 2005258891 | 9/2005 |

(Continued)

OTHER PUBLICATIONS

Verkruysse, W., et al.; Remote plethysmographic imaging using ambient light; 2008; Opt Express; 16(26) 21434-21445.

*Primary Examiner* — Joel Lamprecht

(57) ABSTRACT

The present disclosure relates to the measurement of vital signs such as a respiratory rate or a heart rate. In particular, a system (1) for determining a vital sign of a subject (100), comprising an imaging unit (2) for obtaining video data of the subject, a marker (10, 20, 60, 61) directly or indirectly attached to a body of the subject, wherein the marker comprises a graphical pattern (11, 21), an image processing unit (3) for detecting said marker in said video data, and an analysis unit (4) adapted to extract a vital sign parameter related to the vital sign of the subject from said video data and to determine the vital sign from said vital sign parameter. Further aspects of the disclosure relate to a device and (Continued)

a method for determining a vital sign of a subject and a computer program for carrying out said method.

20 Claims, 7 Drawing Sheets

(51) Int. Cl.
*A61B 5/024* (2006.01)
*A61B 5/08* (2006.01)
*A61B 5/11* (2006.01)
*A61B 5/113* (2006.01)
*A61B 90/00* (2016.01)
*A61B 5/117* (2016.01)

(52) U.S. Cl.
CPC ........ *A61B 5/02427* (2013.01); *A61B 5/0816* (2013.01); *A61B 5/113* (2013.01); *A61B 5/1127* (2013.01); *A61B 5/441* (2013.01); *A61B 5/7278* (2013.01); *A61B 90/39* (2016.02); *A61B 5/117* (2013.01); *A61B 5/7207* (2013.01); *A61B 2090/3937* (2016.02)

(56) References Cited

U.S. PATENT DOCUMENTS

| | | |
|---|---|---|
| 2003/0149353 A1 | 8/2003 | Boos |
| 2006/0025660 A1 | 2/2006 | Swedlow et al. |
| 2007/0076935 A1 | 4/2007 | Jeung et al. |
| 2008/0149701 A1 | 6/2008 | Lane |
| 2008/0221399 A1* | 9/2008 | Zhou .................... A61B 5/021 600/301 |
| 2011/0223078 A1 | 9/2011 | Ohashi |
| 2012/0022348 A1 | 1/2012 | Droitcour et al. |
| 2013/0035599 A1 | 2/2013 | De Bruijn et al. |
| 2013/0267838 A1* | 10/2013 | Fronk .................... A61B 5/066 600/424 |
| 2014/0221847 A1 | 8/2014 | Dubielczyk et al. |
| 2014/0243648 A1 | 8/2014 | Dubielczyk |
| 2016/0045114 A1* | 2/2016 | Dacosta ............... A61B 5/0059 600/476 |

FOREIGN PATENT DOCUMENTS

| | | |
|---|---|---|
| JP | 2007319347 | 12/2007 |
| WO | 2012093311 A1 | 7/2012 |

* cited by examiner

-prior art-

SYSTEM FOR CAMERA-BASED VITAL SIGN MEASUREMENT

CROSS REFERENCE TO RELATED APPLICATIONS

This application is a national filing of PCI application Serial No. PCT/IB2013/054764, filed Jun. 11, 2013, published as WO 2013/186696 A1 on Dec. 19, 2013, which claims the benefit of U.S. provisional application Ser. No. 61/658,538 filed Jun. 12, 2012 and U.S. provisional application Ser. No. 61/739,770 filed Dec. 20, 2012, both of which are incorporated herein by reference.

FIELD OF THE INVENTION

The present invention relates to a system, device, method and computer program for determining a vital sign, in particular a respiratory rate, of a subject.

BACKGROUND OF THE INVENTION

Vital signs of a person, for example the heart rate (HR) or respiratory rate (RR), can serve as a powerful predictor of serious medical events. For this reason, the respiratory rate is often monitored online in intensive care units or in daily spot checks in the general ward of a hospital. A non-invasive respiratory rate measurement can be accomplished optically with the help of a stationary video camera.

A video camera captures the breathing movements of a patient's chest in a stream of images. The breathing movements lead to a temporal modulation of certain image features, wherein the frequency of the modulation corresponds to the respiratory rate. Examples of such image features are the average amplitude in a spatial region of interest (ROI) around the patient's chest, or the location of the maximum of the spatial cross-correlation of the ROI in subsequent images. The quality and reliability of the obtained vital sign information is largely influenced by the quality of the input video data, in particular the image contrast and the appropriate selection of the ROI. In particular, a manual selection of the ROI is time-consuming. Further, movements of the patient that are not related to vital signs disturb the measurement.

EP 2 380 493 A1 discloses a respiratory motion detection apparatus for detecting the respiratory motion of a person. An illuminator illuminates the person with an illumination pattern and a detector detects the illumination pattern on the person over time. The illumination pattern deforms significantly with slight movements of the person. This deformation is analyzed over time in order to determine the respiratory movement of the person. The area of pattern projection has to be adjusted on the patient, preferably on the patient's chest. The disclosed apparatus increases the reliability of the respiratory rate measurement at the additional cost of an active illumination unit for pattern projection.

SUMMARY OF THE INVENTION

It is an object of the present invention to provide a system, device and method for more accurate and reliable vital sign measurements at reduced system cost.

In a first aspect of the present invention, a system for determining a vital sign of a subject is presented that comprises an imaging unit for obtaining video data of the subject, a marker attached to a body of the subject, wherein the marker comprises a graphical pattern, an image processing unit for detecting said marker in said video data, and an analysis unit adapted to extract a vital sign parameter related to the vital sign of the subject from said video data and to determine the vital sign from said vital sign parameter.

In a further aspect of the present invention a device for determining a vital sign of a subject is presented that comprises an imaging unit for obtaining video data of the subject, an image processing unit for detecting a marker in said video data, wherein said marker is attached to a body of the subject, wherein the marker comprises a graphical pattern, and an analysis unit adapted to extract a vital sign parameter related to the vital sign of the subject from said video data and to determine the vital sign from said vital sign parameter.

In a further aspect of the present invention a method for determining a vital sign of a subject is presented that comprises the steps of attaching a marker to a body of the subject, wherein the marker comprises a graphical pattern, obtaining video data of the subject, detecting said marker in said video data, extracting a vital sign parameter related to the vital sign of the subject from said video data, and determining the vital sign from said vital sign parameter.

In yet another aspect of the present invention, there is provided a computer program which comprises program code means for causing a computer to perform the steps of the method for determining a vital sign of a subject when said computer program as carried out on a computer.

Preferred embodiments of the invention are defined in the dependent claims. It shall be understood that the claimed device, methods and computer program have similar and/or identical preferred embodiments as the claimed system and as defined in the dependent claims.

The term 'vital sign' as used herein refers to a physiological parameter of a subject. In particular, the term 'vital sign' comprises the heart rate (HR), the respiratory rate (RR), body temperature, blood pressure, the concentration of a substance in blood and/or tissue, such as an oxygen saturation or a glucose level.

Prior art systems can be grouped into passive systems without active illumination and active systems, such as EP 2 380 493 A1, with an active illumination source for pattern projection.

The inventors have found that passive systems according to prior art fail to produce reliable vital sign measurements. In particular, voluntary movements of the patient, i.e. movements that are not related to vital signs, cause changes in the image of the scenery that can be misinterpreted as a pathologic condition of the patient. Moreover, prior art systems show a limited measurement performance at low image contrast i.e. when measuring a patient underneath a single-color blanket or at low light levels.

Furthermore passive prior art systems only evaluate a motion in the two-dimensional image or video stream. Hence, a respiratory movement of significant amplitude that occurs predominantly in a movement direction perpendicular to the image plane can be misinterpreted as shallow breathing. In other words, only movement directions in the image plane produce reliable measurement data with significant amplitude.

The marker according to the present invention comprises a graphical pattern. This graphical pattern enables the system to determine the orientation and/or location of the marker. This orientation can be used to transfer the two-dimensional video data into a three-dimensional movement of the marker. Hence, a low amplitude in the image plane can be reconstructed to its actual amplitude in the three-dimensional space of the patient. This significantly improves measurement performance and reduces the amount of false respiratory alarms that alert a doctor.

The marker according to the present invention can be used in vital sign measurements directly or indirectly. Firstly, the marker directly defines the region of interest to be measured. For respiration measurements, the movement of the marker itself can be directly evaluated. For example the marker is placed on a patient's chest. The respiratory movement of the chest (and marker) is directly tracked to determine the respiratory rate. Alternatively, for a heart rate measurement, the color change over time of the skin at the marker is evaluated.

Secondly, the marker can be used indirectly as an indicator that indicates a region of interest (ROI) to be evaluated. For example, the marker is placed on the upper arm of the patient next to the chest. In this example, the marker does not move substantially. However, the ROI is located at a known position relative to the marker. Hence, the orientation and position of the marker indicate which region of the image has to be evaluated for the determination of vital signs. Still further, the orientation and location of the ROI can be estimated in order to project a measured amplitude of a vital-sign-related movement in the two-dimensional image plane into three-dimensional space. This knowledge about the actual movement direction and movement amplitude of the vital sign also allows determining a reliability metric of the measured vital sign.

Active systems, such as EP 2 380 493 A1, are capable of producing reliable measurement results, however, at the additional cost of and active illumination unit for pattern projection. The system according to the present invention is a passive system that is less expensive because it does not require an active illumination unit. Furthermore system complexity is reduced which benefits maintenance.

The marker comprises a graphical pattern adapted to be detectable by the image processing unit in the video data. Preferably, the marker is a graphical pattern with high image contrast, for example black and white pattern. Alternatively, the graphical pattern comprises different colors that can be clearly distinguished. Favorably, the graphical pattern is optimized to be machine-readable such as a barcode, a matrix barcode, alphanumerical characters or QR-code or the like. Favorably, a graphical pattern is used that is optimized for detectability. For the image processing unit it is easier to detect a specified graphical pattern in the observed scene than making an intelligent decision on which region of interest is an optimal site for the measurement.

In a first embodiment of the present invention, said vital sign parameter is a respiratory movement and the determined vital sign is a respiratory rate.

In a second embodiment of the present invention, said vital sign parameter is a temporal variation of the skin color and the determined vital sign is a heart rate or pulse. The color of the skin comprises the brightness and the spectrum. For determining the heart rate or pulse, it is sufficient to evaluate the temporal variation of the brightness. Optionally, the brightness of several spectral components, for example the RGB (red, green, blue) channels of a color camera is evaluated. The skin color to be analyzed is not limited to the visible spectrum. Several spectral components, including the infrared, can be evaluated to determine additional values such as a blood oxygen saturation or a glucose level. In general the spectral evaluation enables a remote measurement of a concentration of a substance in blood and/or tissue.

According to another embodiment of the present invention, the marker further comprises an orientation indicator for indicating the orientation of the marker. The orientation indicator can be a part of the graphical pattern or a separate element on the marker. In a hospital, the marker is typically attached to the body of the patient by a nurse or other medical personnel. In one example, the orientation indicator indicates how the marker should be attached to the body of the subject. This is important because then the imaging unit can be adapted to measure movements in specific directions with respect to the patient and/or marker.

Respiration movements are ideally measured perpendicular to the chest surface. The orientation indicator can, for example, be implemented as a pictogram or arrow. Alternatively, the orientation and/or location of the marker can be determined from the graphical pattern, for example by providing a machine-readable pattern that allows the determination of the location and/or orientation of the marker in the video data by the image processing unit.

In a further embodiment of the present invention, the marker is comprised in a substantially planar surface. In particular, the marker is a substantially two-dimensional object. For example, the marker with the graphical pattern and orientation indicator can be printed on a type of "mouse pad" that can be placed on a patient's chest. Alternatively, the marker can be printed on a piece of paper. A thin substantially two-dimensional marker may, of course, adapt to the shape of the object on which it is placed. For example, the marker may follow the curvature of the patient's chest. This allows for patient-specific markers at very low cost.

According to another embodiment of the present invention, the marker is arranged on a fabric that is adapted to contact the subject or on an item, preferably a medical item, that is adapted to contact the subject. The marker can be printed onto or woven into a blanket, a bed-sheet, T-shirt, romper suit or clothing or similar items. The tracking of a marker printed on blankets allows for near continuous monitoring of the subject while in bed.

Alternatively, the marker is arranged on an item that is adapted to contact the subject. In general, any item can be used that has a fixed or at least relatively fixed position with respect to a region of interest of the subject to be evaluated. Examples include but are not limited to any type of fixture worn by the patient, bed, cast or medical measurement equipment. The graphical pattern can also be manually drawn, rubber stamped or printed on the surface of interest, including the patient's skin.

In order to increase workflow efficiency, the marker comprising a graphical pattern can be added to other items that are used in treatment of the patient already, such as a hospital gown or a blood pressure cuff.

In another embodiment of the present invention, the marker at least partially covers a region of interest of the body of the subject which suits for deriving the vital sign. As an example, the marker is placed on the patient's chest. Hence, the marker covers a region of the body that moves up and down during the respiratory cycle. As a further example, the marker is placed on the patient's forehead to determine the heart rate from the color change of the skin at the marker. An at least partially transparent marker or a marker with openings can be used to image the bare skin underneath the marker. The evaluated region in the video data can also be selected larger or smaller than the size of the marker.

According to another embodiment of the present invention, the marker is positioned on or adjacent to the chest of the subject. When positioned directly on the chest of the subject, the movement of the marker can be directly evaluated. Alternatively, the marker is positioned adjacent to the chest such as on a blood pressure cuff or other item carrying said marker. In this case, the marker is detected in the video data to determine the position of the item carrying the marker. The region of interest (ROI) for extraction of vital sign parameters is then selected relative to the position of the marker.

According to another embodiment of the present invention, the analysis unit is calibrated using a location and/or orientation of the marker attached to the body of the subject. The video data obtained by the imaging unit is a series of two-dimensional images. The marker comprising a graphical pattern is imaged by this imaging unit. In other words, the graphical pattern is a known two-dimensional element that is projected onto the image plane. The analysis unit can now determine the orientation and/or location of the marker in three-dimensional object space, i.e. in the space in front of the camera, based on the known graphical pattern of the marker and the projected image. For example, the imaging unit is oriented at an angle of 45° with respect to the direction of a respiratory motion of the patient. The direction of respiration is defined as the movement direction substantially perpendicular to the chest of the patient that occurs during inhaling or exhaling. The analysis unit can determine this angle from the projection of the marker in the image video data. Hence, a projected movement of the chest of 4 cm at 45° angle corresponds to an actual movement of 5.6 cm in the direction of respiration. In general, certain particular image features may have a directional characteristic, for example, they may produce a maximum signal amplitude for motions in a particular spatial direction, which can be chosen in accordance with the predominant motion components. The analysis unit can be further adapted to correct for a deformation of the marker e.g. a curvature of a flexible marker when placed on a patient's chest. Alternatively a rigid marker is used.

The orientation and/or location of the marker can further help to determine the relative location to be evaluated for vital sign measurement. The orientation and/or location of the marker can be used to determine where the vital sign parameter can be expected in the video data. In a first example, the marker is placed on a blood pressure cuff that is attached to the arm of the patient. During a blood pressure measurement, the arm of the patient is typically located next to the chest. The image processing unit detects said marker in the video data and determines the chest, as the region of interest for evaluation of vital sign, as a position relative to the location and orientation of the marker. The respiratory rate is then determined from a respiratory movement of the ROI. Alternatively, the position of the face of the patient can be estimated from the position and/or orientation of the marker on the blood pressure cuff. A temporal variation of the skin color of the face can be evaluated to determine the heart rate of the patient.

In another embodiment of the present invention, the image processing unit is adapted to determine a measurement quality metric. The system provides a nurse with feedback about how well marker and camera are positioned. In particular the orientation and/or location of the marker with respect to the imaging unit can be used as a feedback to the nurse to adjust the position of the imaging unit for optimum measurement signal quality. For example, the direction of a respiratory movement should comprise at least a motion component perpendicular to the image plane.

According to a further embodiment of the present invention, the marker further comprises encoded data. For contactless measurements there is no physical link between the measurement system and the subject being monitored. However it is crucial for a monitoring system to make sure that the information acquired by the measurement system is correctly assigned to the monitored subject. Encoded data can therefore include patient-related data such as the patient's name, hospital ward, a patient identifier. Based on this information, the determined vital sign can be directly and automatically assigned to a health record of the patient. Furthermore the parallel measurement of the vital sign and of the patient identifier provides an inherently safe system that ensures that the measurement values are correctly assigned to the right patient. This also simplifies the workflow. In an embodiment, multiple markers are attached to a patient in order to obtain multiple vital sign measurements from different body parts. For example the oxygen saturation is measured at the forehead and at both hands.

Markers with encoded data can also be used to identify multiple subjects or multiple desired measurement sites at the subject's body. The encoded data could be a unique identifier code which allows the image processing unit to automatically pick a particular marker out of several markers. Several patients, for example each wearing a T-shirt with a distinct marker, can be monitored at the same time. Furthermore a patient can be automatically recognized when moving around the hospital, for example, while being transferred from one room to another. Still further, the encoded data can be patient specific, e.g. weight, height, etc. which can aid the identification of a patient or alternatively help in determining an appropriate region of interest for extraction of vital sign parameters.

Markers with encoded data can also provide information for supporting the vital sign measurement, for example calibration data. Calibration data comprises calibration adjustments depending on the subject or for one subject depending on the body part from which the measurement is to be taken. The calibration data can comprise a mathematical calibration function, which is used in determining the vital sign, and/or coefficients for use by a calibration function. Alternatively, the calibration data comprises placement information, for example placement on the forehead, arm, leg, cheek, and the system queries a database to obtain the calibration information to configure the system for measuring a vital sign at the place that is indicated by the placement information. Furthermore, the calibration data comprises information for controlling a light source to illuminate the subject. For example an infrared light source, or light source with a defined emission spectrum, is switched on or the intensity is adjusted based on the calibration data.

In a further aspect of this embodiment, the marker further comprises encoded data for configuration of a measurement accuracy of the system. Depending on the application scenario there are different requirements for the measurement accuracy. For example for an oxygen saturation measurement on ventilated neonates it is important to accurately determine the oxygen saturation in the range of 90-100%, while in a general ward scenario it can be sufficient to distinguish between a healthy oxygen saturation of 95-100% a low oxygen saturation of 60-85%. Furthermore, for some applications a trend measurement without any requirements on the absolute measurement values is sufficient. The coding of the required accuracy and/or application into the marker can be used to automatically select different thresholds for issuing a warning or notification and thereby avoid unnecessary alarms.

Encoding data on the marker is especially beneficial if the system for determining the vital sign of the subject is a stand-alone system. For example a patient identifier, calibration data or a required accuracy can be provided to the system without connection to an external entity such as a medical information system or an electronic health record.

The graphical pattern comprising the encoded data can be any type of machine readable code, for example, a QR code, a barcode, machine readable alphanumeric characters or sequences, a pictogram or a geometrical pattern, including a size and/or shape of the marker, an arrangement of openings in the marker, in black and white or having a single or different colors.

Furthermore, an error correction code can be used or encryption applied for patient privacy. The encoded data can be further used to verify markers from the original equipment manufacturer.

As a synergetic effect, the encoded data can be used to determine a measurement quality metric. The encoded data can be encoded using an error detection or error correction code. Based on the number of errors during detection a measurement quality metric can be established. In other words, the encoded information can also be used to determine the reliability, confidence or quality of the vital sign measurement.

In another embodiment, the system according to the present invention further comprises a second imaging unit for obtaining second video data of the subject and a second image processing unit for detecting said marker in said second video data. An advantage of a second imaging unit is that the reliability of the determination of the vital sign of the subject can be improved. The second image processing unit detects the marker in the second video data and thereby enables an alignment of images comprised in the video data and of second images comprised in the second video data. The marker helps that the same region of interest is evaluated in both video streams. Optionally, the imaging units are mounted at different positions with respect to the subject to provide measurements from different perspectives. Optionally more than two imaging units and image processing units can be used. Furthermore the function of two or more individual image processing units can be implemented as one image processing unit.

In a further embodiment of the system, the imaging unit comprises a filter for selectively transmitting light at a first wavelength and the second imaging unit comprises a second filter for selectively transmitting light at a second wavelength. For example, the first imaging unit is a video camera with a filter for red wavelengths and the second imaging unit is a second video camera with a second filter for infrared wavelengths. The measurement at different wavelengths enables the measurement of a concentration of a substance in blood and/or tissue, for example for remotely determining the blood oxygen saturation. Additional wavelengths can be evaluated with further imaging units with appropriate filters.

The term 'wavelength' as used herein also refers to a wavelength band or wavelength range. For example the term wavelength refers to the emission spectrum of a light source and does not only comprise the center wavelength. Accordingly, for an optical filter the term wavelength refers to a pass band of the filter. Hence, the term wavelength is not limited to one single wavelength but is also used for a wavelength range, for example of some nanometers or some tens of nanometers, around a center wavelength.

In a further embodiment of the system according to the present invention, the graphical pattern of the marker is invisible to the subject. For example, the marker can only be detected by an infrared camera. Alternatively, the marker comprises a combination of visible and invisible features. For example, an invisible graphical pattern is combined with a visible orientation indicator. The visible orientation indicator instructs the nurse how to place the marker, while the invisible graphical pattern can be monitored using an infrared camera even if the patient is asleep. Visible and/or infrared light sources can be applied to ensure sufficient lighting and image contrast.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
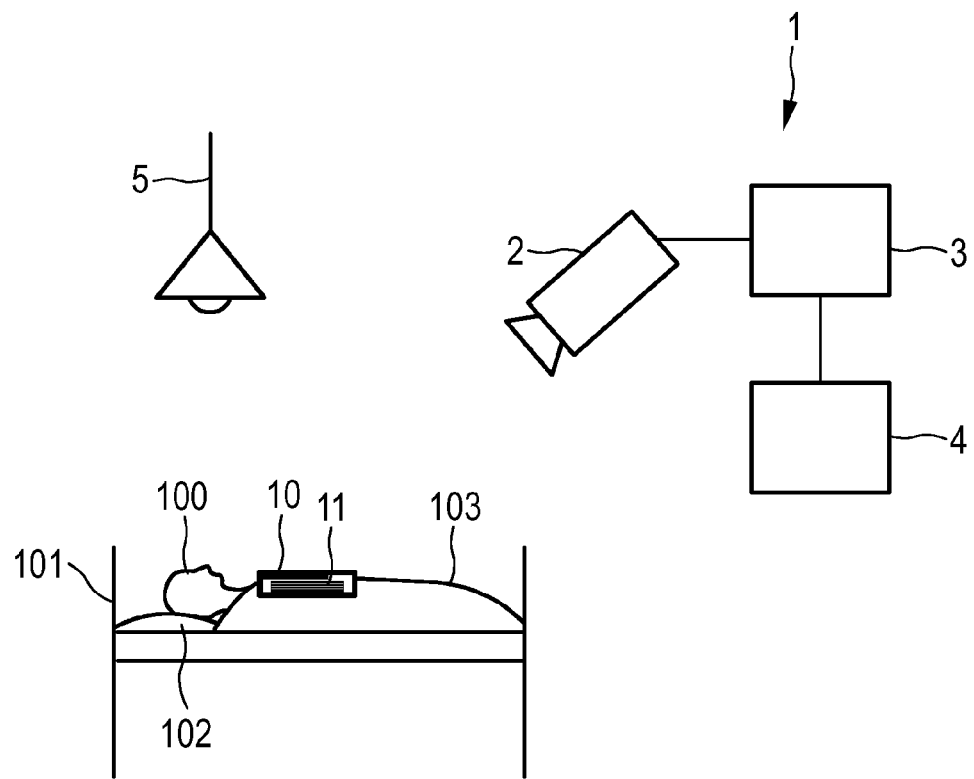
FIG. 1 shows an exemplary embodiment of the system for determining a vital sign of a subject according to the present invention.

FIG. 1 shows an exemplary embodiment of a system 1 for determining a vital sign of a subject 100 according to the present invention. The subject 100 lies in a bed 101, wherein the head of the subject 100 is located on a pillow 102 and the subject 100 is covered with a blanket 103. The system 1 comprises an imaging unit 2 for obtaining video data of the subject 100 and a marker 10 attached to a body of the subject 100. The marker 10 comprises a graphical pattern 11. An image processing unit 3 is adapted to detect said marker 10 in the video data. An analysis unit 4 is adapted to extract a vital sign parameter related to a vital sign of the subject 100 from the video data and to determine a vital sign from the vital sign parameter. In this example, the vital sign parameter is a respiratory movement and the vital sign is a respiratory rate.

The marker 10 is directly attached to the body of the subject 100 by placing it on the chest of the subject 100. In this example, the marker 10 is printed onto the blanket 103.

The imaging unit 2 is installed at a remote distance, for example, at a ceiling or a wall of a room in which the bed 101 is located. A lamp 5 can be present to illuminate the scene and to ensure sufficient image contrast. In one embodiment, the imaging unit 2 can be an infrared camera, and the light source 5 can be an infrared light source.

The orientation of the patient 100 with respect to the imaging unit 2 is determined automatically from the orientation of the graphical pattern 11 on the marker 10.

Figure 2:
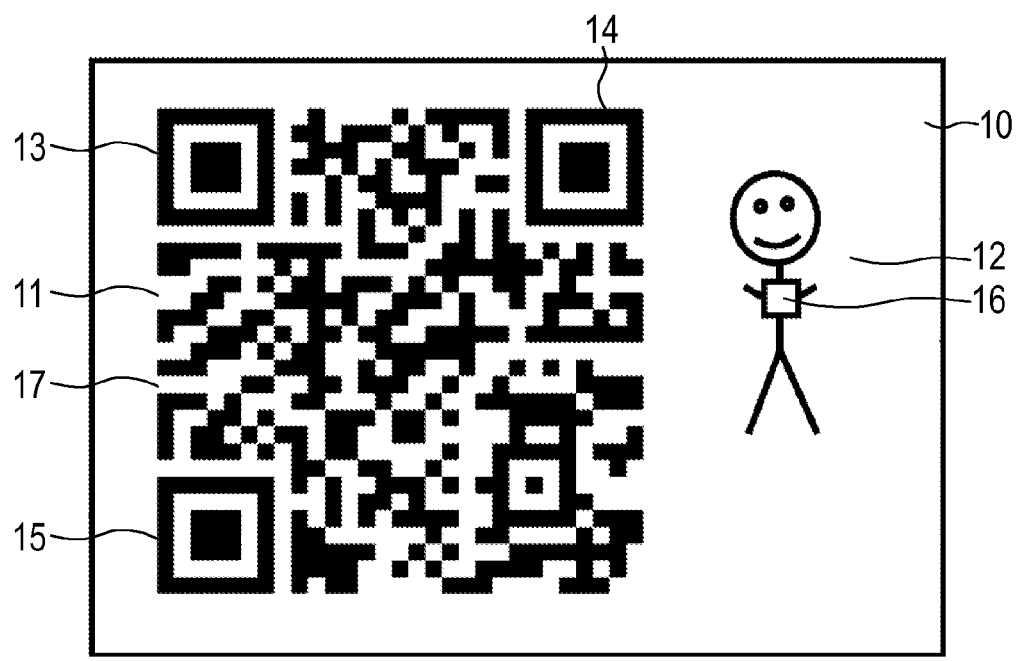
FIG. 2 shows a first example of a marker with graphical pattern.

FIG. 2 shows a first embodiment of the marker 10 comprising a graphical pattern 11 and an orientation indicator 12 for indicating the orientation of the marker. In this example, the graphical pattern 11 is a so-called QR-code 17. The QR-code features three structural elements 13, 14, 15 which allow for a machine-readable determination of the orientation and/or location of the pattern 11. In order to facilitate correct placement of the marker 10 on the body of the subject 100, an additional orientation indicator 12 can be implanted alongside with the graphical pattern 11. In this example, the orientation indicator is a pictogram of a person that shows the position 16 where to place the marker 10.

The marker 10 can be made out of paper, cloth, rubber, or a similar material. As an example, one may picture a computer mouse pad, which has a rubbery bottom surface which keeps it from sliding. The graphical pattern 11 will then be printed on the top surface of the "mouse pad". The marker 10 may also have defined weight to ensure that it follows to breathing motions closely.

The graphical pattern 11 can be generated through a computer program and can be printed on the material. In case of the QR-code, patient specific data can be encoded along with error protection or encryption of the data. Alternatively, other types of machine-readable graphical patterns can be employed.

Figure 3:
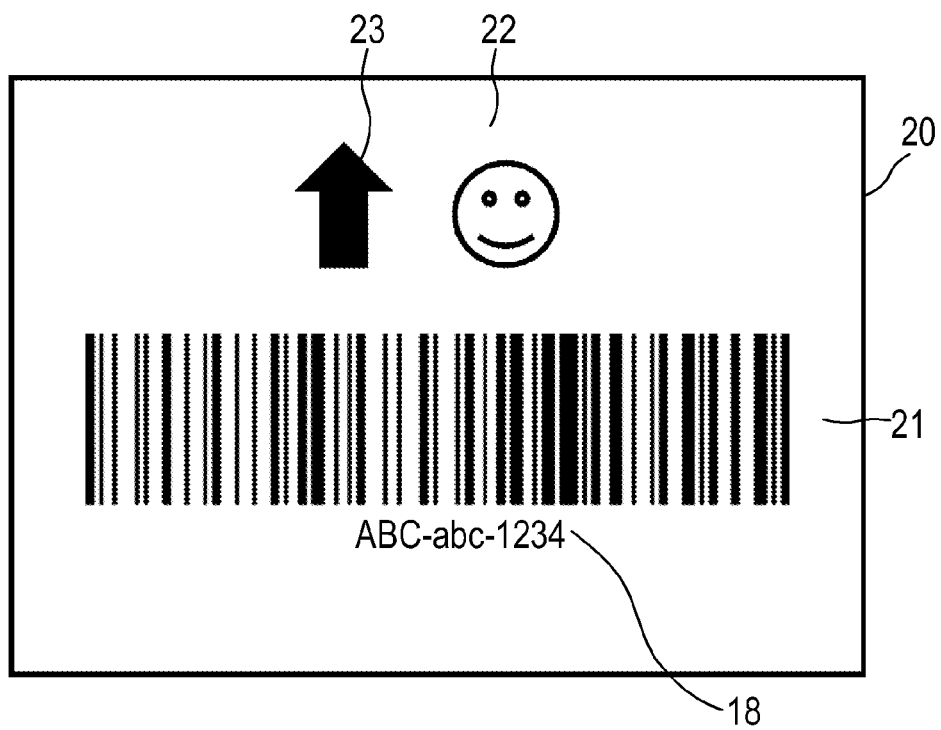
FIG. 3 shows a second example of a marker with graphical pattern.

FIG. 3 shows an alternative embodiment of the marker 20 with a graphical pattern in form of a barcode 21. Furthermore, the marker 20 comprises an orientation indicator with an arrow 23 and a pictogram 22 of a face that has to be aligned so as to point at the face of the subject 100. Data is encoded in the barcode 21 and printed as text 18.

Figure 4:
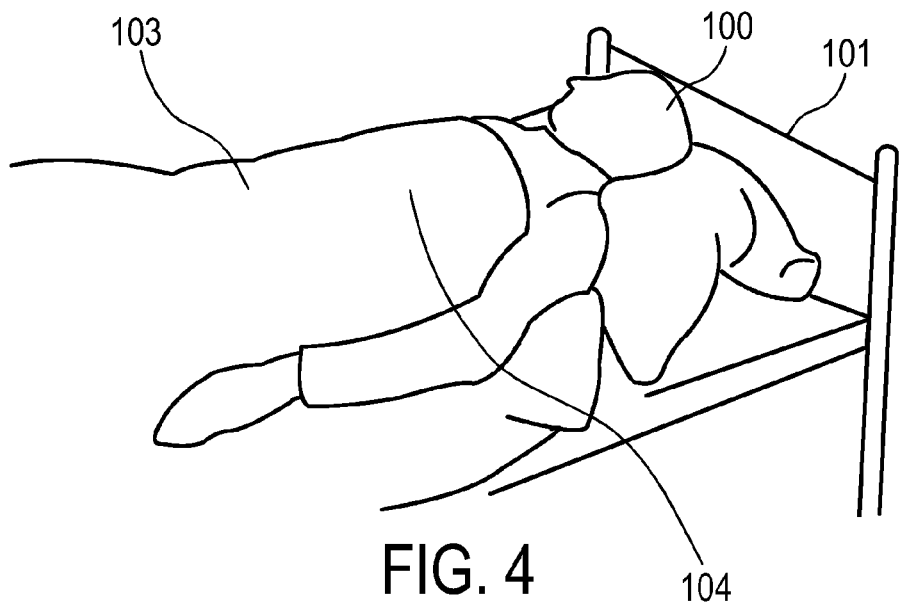
FIG. 4 shows a measurement scenario according to the prior art.

FIG. 4 shows a measurement scenario according to the prior art. The subject 100 is monitored while sleeping in bed 101. The subject 100 is covered by a white blanket 103. A video sequence of this scene is analyzed to determine the respiratory rate of the patient 100. An analysis of the entire image also includes movements of the patient that are not related to respiratory movements and cause measurement errors.

In another known example, the nurse manually selects the area of the video that corresponds to the chest 104 of the subject 100. This region of interest (ROI) is then analyzed for periodic movements corresponding to the respiratory rate of the subject 100. This procedure is time consuming and prone to errors.

Figure 5:
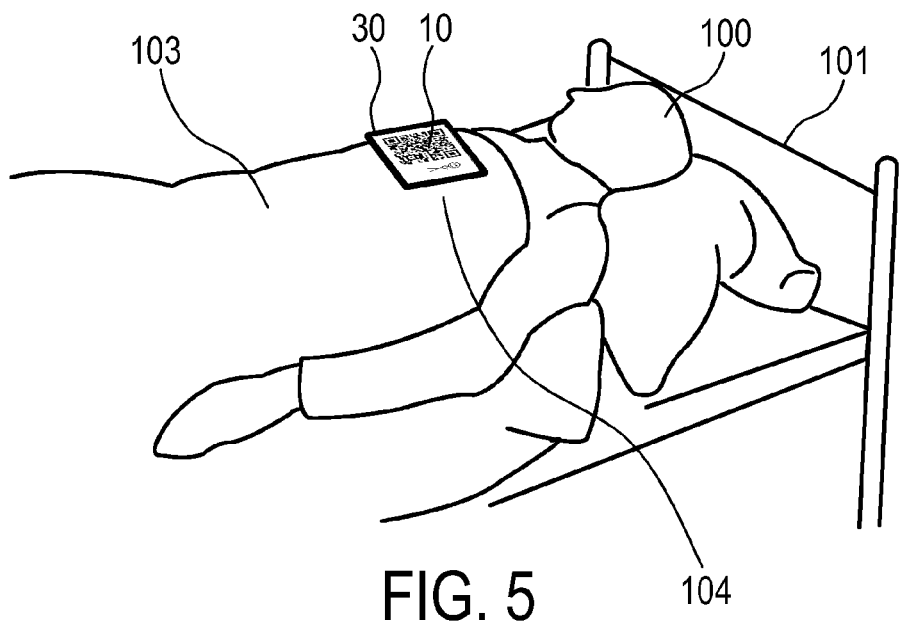
FIG. 5 shows a measurement scenario according to the present invention.

FIG. 5 shows a measurement scenario using the system for determining a vital sign of a subject 100 according to the present invention. In contrast to FIG. 4, FIG. 5 shows a marker 10 placed on the chest 104 of the subject 100. The marker 10 comprises a machine-readable graphical pattern 11 that can easily and automatically be detected by the image processing unit 3 according to the present invention. The code pattern 11 can further include encoded data that gives instructions to the system for determining vital signs about how to select the region of interest. For example, the region of interest (ROI) 30 can be selected as large as the marker 10 itself. Alternatively, the encoded data can provide instruction to set the size in one or two dimensions of the marker 10 smaller or larger than the marker 10 itself. Alternatively, markers of different size can be made available. Instead of selecting a size of the ROI on the computer, a marker 10 of appropriate size can be placed on the chest of the patient 100. For example, a larger marker 10 is used for an adult, whereas a smaller marker 10 is used for a child.

The graphical pattern 11 on the marker 10 allows for an automatic determination of the orientation and location of the marker 10. The graphical pattern 11 is fixed and does not change from image to image in the video data obtained from the imaging unit 2. Hence, a movement of this marker can easily be tracked. An imaging unit 2 refers to any type of image source producing a plurality or stream of images such as a camera.

In a preferred embodiment, the movement of the marker 10 includes at least one movement component perpendicular to the imaging unit 2. This allows for easy motion tracking. In an alternative embodiment, the marker 10 can also be used to estimate the distance between the camera 2 and the marker 10. This information can be used as a feedback to the nurse to adjust the camera's position for optimum measurement signal quality. Feedback can be provided on a display indicating the signal strength. Alternatively acoustical feedback is provided, so that the nurse can adjust the marker 10 while still facing the patient 100.

Figure 6:
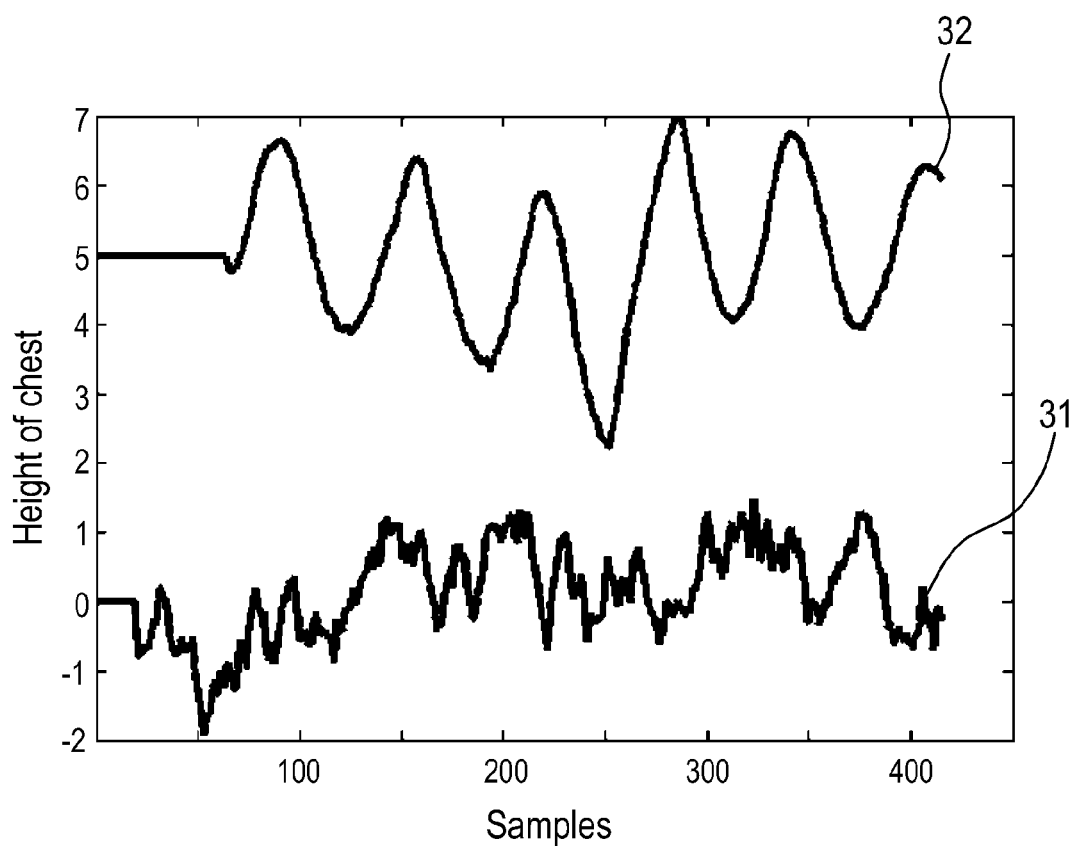
FIG. 6 shows an example graph of movement of the subject.

FIG. 6 shows the improvement in measurement data that can be achieved with the device 1 according to the present invention (FIG. 5) in comparison to prior art (FIG. 4). Here, a mechanical phantom was used to simulate the respiratory movements for a fair comparison between the measurement curves according to prior art 31 and according to the present invention 32. The response of a feature detector is shown for a region of interest on a bed-sheet 31 and for a region of interest with the QR-pattern-based marker 32. The device according to the present invention produces a greatly improved signal which clearly displays the breathing cycles and improves the subsequent respiratory rate estimation. Furthermore, the orientation and location of the marker can be considered in the extraction of the vital sign parameter. For example, a projection of marker that is tilted with respect to the image plane can be corrected for by adjusting the amplitude of the graph. Hence, the system according to the present invention gives an absolute amplitude of the respiratory movement.

Figure 7:
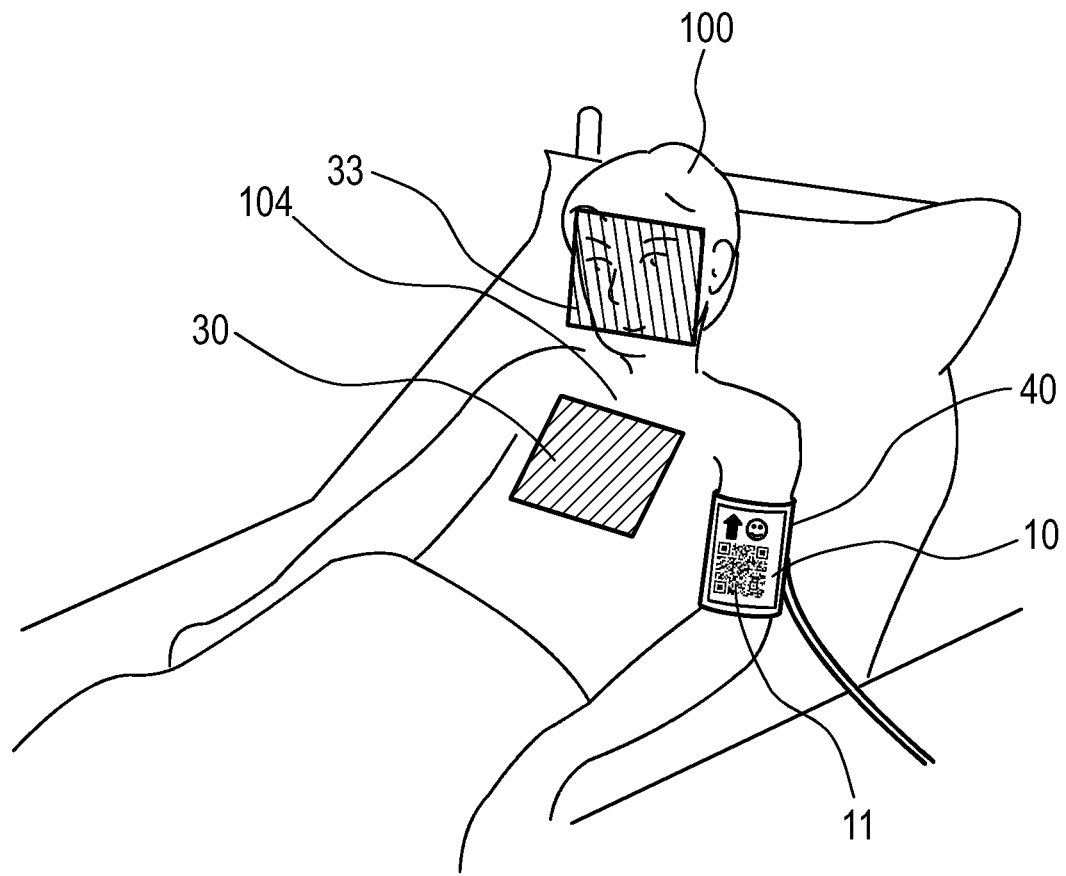
FIG. 7 shows an alternative embodiment of the present invention with the marker integrated into a blood pressure cuff.

FIG. 7 shows an alternative embodiment of the present invention during a standard spot-check procedure in the general ward. In this procedure, the nurse applies a blood pressure cuff to one of the patient's arms. During the blood pressure measurement, the patient 100 is generally instructed to be quiet and not to move. These are ideal conditions for a simultaneous measurement of the breathing rate using a camera. The marker 10 on the cuff 40 will aid the camera to automatically find the correct ROI 30 for the breathing rate measurement on the patient's chest 104.

More specifically, at the beginning of the blood pressure measurement, the pattern on the cuff 40 can be automatically found in the camera image, given that the camera is roughly pointed at the patient 100, and that it covers a sufficiently wide field-of-view. Since the cuff 40 is always on one of the upper arms, the position of the cuff 40 and pattern 11 is immediately indicative of the relative location of the patient's chest 104. In other words, the region of interest is located next to the blood pressure cuff 40 at some centimeters distance. The chest 104 can therefore be found easily, robustly, and in a fully automatic manner. The breathing rate measurement can commence undisturbed along with the blood pressure measurement without any additionally required human intervention or action. This can significantly increase the workflow efficiency of the nurse and improve the quality of the breathing rate measurement.

A conventional determination of the respiratory rate is done by manually counting breaths. This is highly error-prone and in practice often circumvented by medical personnel altogether. Research indicates that in practice very often the normal breathing rate of "18" breaths per minute is reported by default by the nurse without any true measurement since such manual counting measurement is time consuming and strenuous.

Furthermore, the patient 100 is not specifically made aware of the breathing rate measurement. Consequently, there is a much reduced danger of the patient 100 to consciously or subconsciously influence his breathing. In other words, the quality of an automatically measured breathing rate is increased.

In an alternative embodiment, the vital sign parameter is a temporal variation of the skin color and the vital sign is a heart rate. FIG. 7 shows the patient's face as a second region of interest 33. Once again, the graphical pattern is automatically detected on the marker 10 by the image processing unit. The marker 10 forms part of a blood pressure cuff 40. In this example, the data encoded in the graphical pattern 11 instructs the system 1 for determining vital signs that the second region of interest 33 is located at a specific distance and orientation from the marker 10. Furthermore the size of the second region of interest 33 is specified. The analysis unit then extracts the temporal variation of the skin color of the ROI 33 from the video data and determines the heart rate.

If the patient moves during a measurement, the image processing unit can detect this movement of the patient 100 and adjust the region of interest 30, 33 accordingly. Furthermore a frequency domain analysis and filtering can be performed to separate signals from vital sign parameters from overall body movements that are not related to vital signs. Alternative processing steps known from signal processing can be applied.

Figure 8:
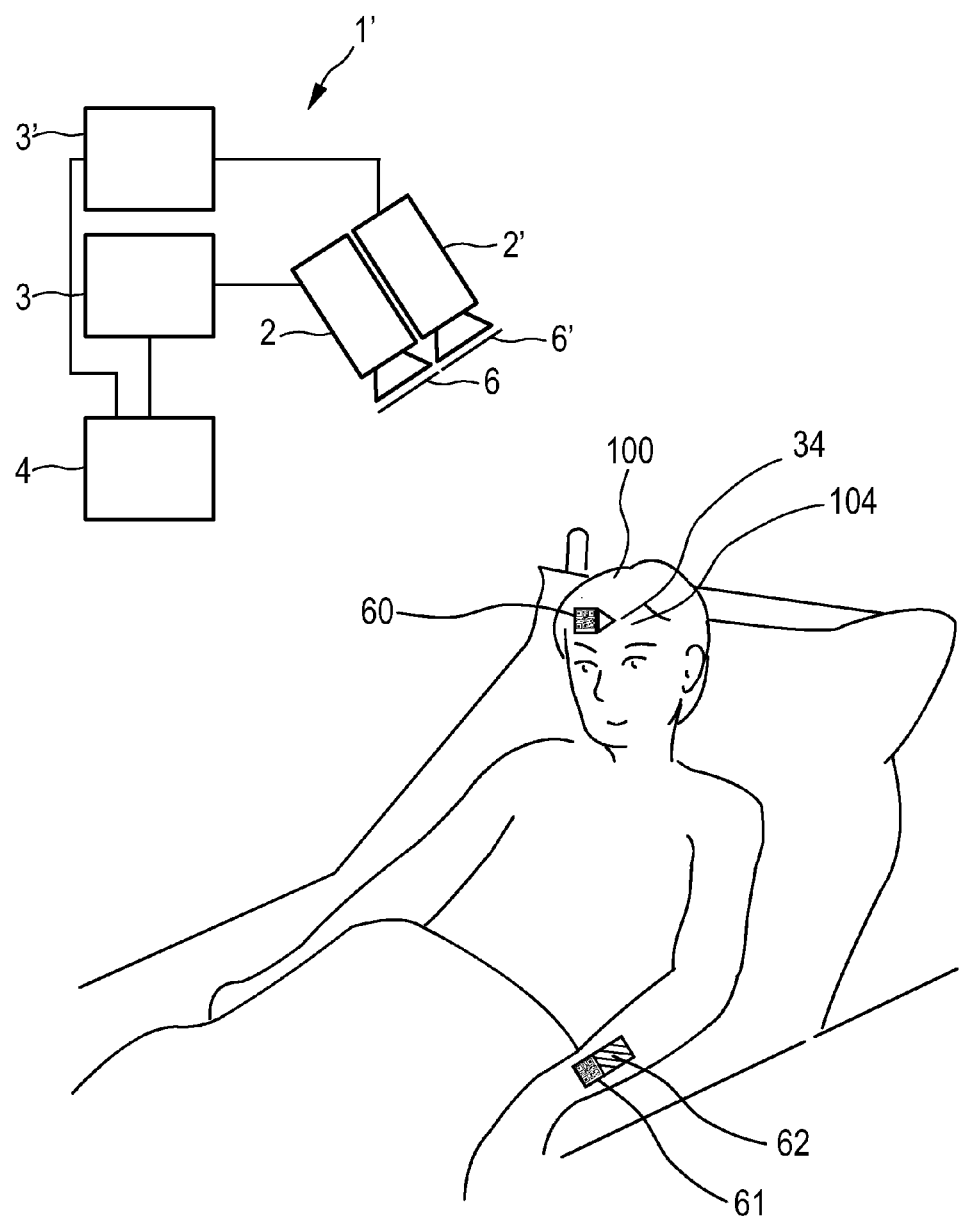
FIG. 8 shows a further embodiment of the present invention with a second imaging unit.

FIG. 8 shows a further exemplary embodiment of a system 1' for determining a vital sign of a subject 100 according to the present invention. The system 1' comprises an imaging unit 2 for obtaining video data of the subject 100, a second imaging unit 2' for obtaining video data of the subject 100, a marker 60 attached to a forehead 104 of the subject 100 and a second marker 61 attached to the left hand of the subject 100. The first imaging unit 2 is a video camera with a filter 6 for selectively transmitting red wavelengths and the second imaging 2' unit is a second video camera with a second filter 6' for selectively transmitting infrared wavelengths.

An image processing unit 3 connected to the imaging unit 2 is adapted to detect said markers 60, 61 in the video data obtained with the imaging unit 2. A second image processing unit 3' connected to the second imaging unit 2' is adapted to detect said markers 60, 61 in the video data obtained with the second imaging unit 2'. The image processing unit 2 and the second image processing unit 2' are connected to an analysis unit 4. The analysis unit 4 is adapted to extract a vital sign parameter related to a vital sign of the subject 100 from the video data obtained with the imaging unit 2 and the second imaging unit 2' and to determine a vital sign from the vital sign parameter. The scene is illuminated with ambient light in a spectral range from the ultraviolet to and including the infrared.

The marker 60 in this example is applied to the forehead 104 of the subject 100. The shape of the marker 60 is a rectangle with a triangle at one side that points towards the central part of the forehead 104 and thereby indicates the region of interest 34 for determining the vital sign of the subject 100. The graphical pattern of the marker 60 is not limited to the shape of the marker 60, but optionally also comprises a machine readable QR code that stores calibration information for the system 1'.

The marker 61 in this example is applied to the left hand of the patient 100. The marker comprises a transparent region 62 next to a machine readable graphical pattern. The skin of the patient 100 can be imaged with the imaging units 2 and 2' through this transparent region 62 of the marker.

In this example, the vital sign is an oxygen saturation of the patient. The oxygen saturation can be determined by evaluating and comparing the temporal variation of the light at red wavelengths and at infrared wavelengths. Because of the red filter 6, the imaging unit 2 only receives light at red wavelengths. Because of the infrared second filter 6', the second imaging unit 2' only receives light at infrared wavelengths. Alternatively other wavelengths are used. The markers 60 and 61 are detected in the video data of the imaging unit 2 and in the video data of the imaging unit 2'. The video data of the two imaging units 2 and 2' can be aligned based on the detected markers. This ensures that the same region of interest is measured at both wavelengths.

The machine readable pattern of the markers 60 and 61 further comprises calibration information. For example, the absorption characteristics of the skin on the forehead 104 and the skin on the hand are different. A calibration curve to account and correct for this difference can be encoded in the graphical pattern of the marker.

Figure 9:
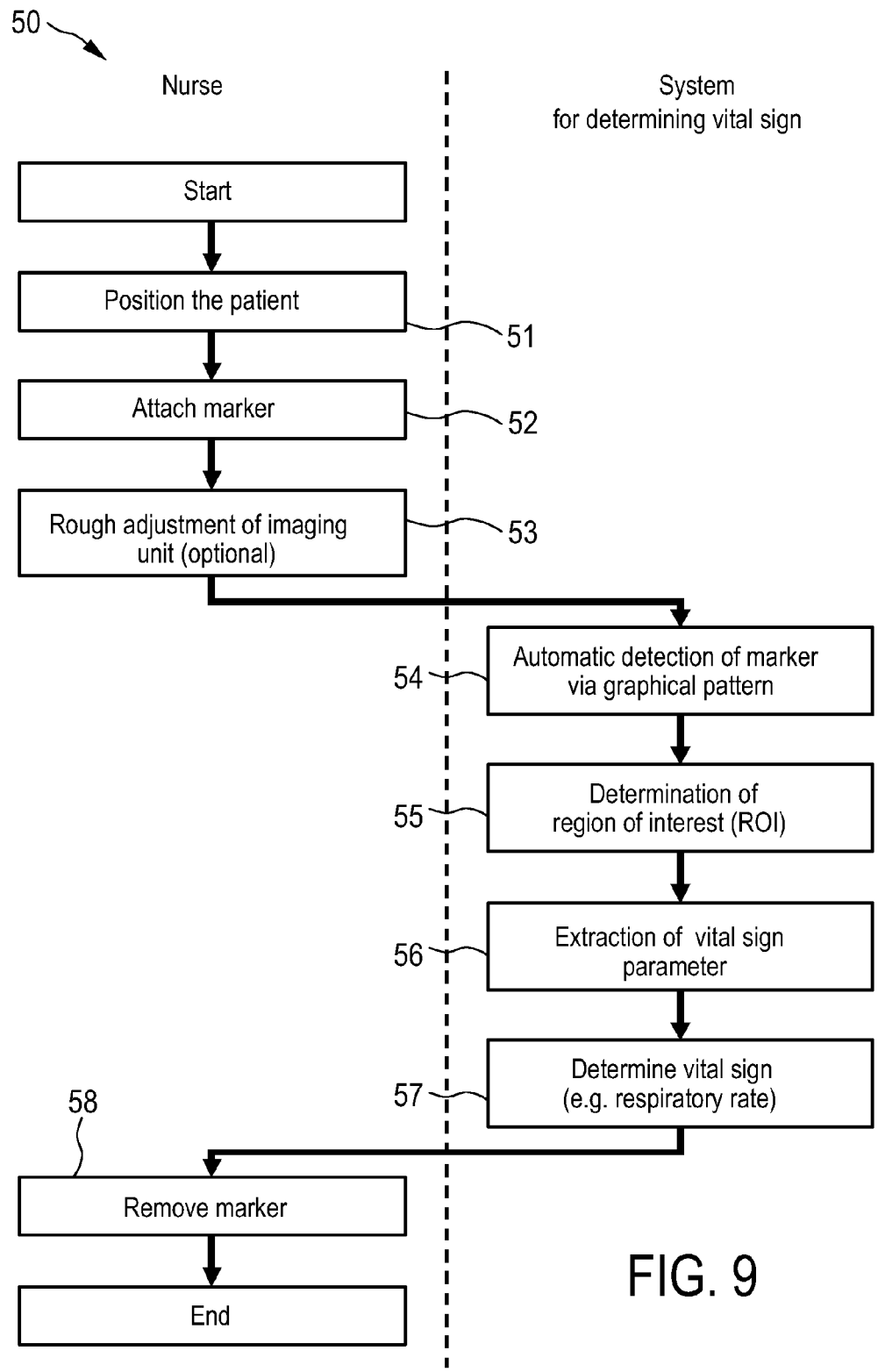
FIG. 9 shows the process flow for measuring a vital sign with the system according to the present invention.

FIG. 9 shows a process flow 50 for determining a vital sign of a subject 100 according to the present invention. Process steps on the left-hand side show steps that have to be performed manually by the nurse. The right-hand side of the graph shows automated process steps carried out by the system according to the present invention. Firstly, the nurse positions 51 the patient on a chair or in a bed and instructs the patient not to move. Next, the marker according to the present invention is attached 52 directly to the region of interest or indirectly for example on a blood pressure cuff attached to the arm of the patient. In a next step 53, the imaging unit is roughly adjusted 53 so that the patient is within its field-of-view. Alternatively an imaging unit with wide angle optics can be used so that no adjustment is necessary.

The system according to the present invention automatically detects 54 the marker via the graphical pattern. The orientation and position of the marker are used to determine 55 the region of interest. Next, the vital sign parameter related to the vital sign of the subject, for example a respiratory movement, is extracted 56 from the video data obtained by the imaging unit. The movement of the subject can then be analyzed to determine the vital sign, for example the respiratory rate, from this movement data. In addition to extracting the periodic movement of the subject related to vital signs, the video data can also be corrected for overall patient movements. For example, an overall movement of the patient outside the region of interest can be tracked and be used to subtract this overall movement of the patient from the movement detected in the region of interest. Hence, only the movement or signal change related to a vital sign such as the respiratory rate is left.

As a last step 58, the nurse only has to remove the marker. It should be noted that the marker can be used again for a different patient.

The measured vital sign information can be automatically provided to a doctor or to a hospital computer system.

The system for determining a vital sign of a subject is intended for use in a hospital, at a clinic, at a doctor or for monitoring patients at home.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A system for determining a vital sign of a subject comprising
   at least one camera configured to obtain video data of the subject,
   a marker attachable to a body of the subject, wherein the marker comprises a machine readable graphical pattern, and wherein the graphical pattern comprises encoded data including information about the subject,
   at least one processor programmed to:
   detect said marker in said video data;
   determine said encoded data from said graphical pattern, and
   extract in dependence of the encoded data a vital sign parameter of the subject from said video data;
   determine a vital sign of the subject from said vital sign parameter; and
   output the vital sign.

2. The system according to claim 1,
   wherein at least one of:
   said vital sign parameter is a respiratory movement of the subject and wherein said vital sign is a respiratory rate of the subject; and
   said vital sign parameter is a temporal variation of a skin color of the subject and wherein said vital sign is a heart rate of the subject and/or a concentration of a substance in blood and/or tissue.

3. The system according to claim 1, wherein the marker further comprises:
   an orientation indicator separate from the graphical pattern for indicating the orientation of the marker.

4. The system according to claim 1,
   wherein the marker is arranged on a fabric that is adapted to contact the subject or a medical item that is adapted to contact the subject.

5. The system according to claim 1,
   wherein the at least one processor is further programmed to:
   extract the information about the subject from the graphical pattern of the marker;
   associate the extracted information about the subject with the extracted vital sign parameter; and
   at least one of:
   display the extracted information and the extracted vital sign parameter; and
   store the extracted information and the extracted vital sign parameter.

6. The system according to claim 1,
   wherein the at least one processor is calibrated using a location and/or orientation of the marker.

7. The system according to claim 1, wherein the at least one processor is programmed to determine a measurement quality metric.

8. The system according to claim 1, wherein the at least one camera includes:
   a first camera configured to obtain first video data of the subject;
   a second camera for obtaining second video data of the subject, and
   wherein the at least one processor is programmed to detect said marker in said first and second video data.

9. The system according to claim 8,
   wherein the first camera comprises a filter for selectively transmitting light at a first wavelength, and
   wherein the second camera comprises a second filter for selectively transmitting light at a second wavelength.

10. A device for determining a vital sign of a subject comprising
    at least one camera configured to obtain video data of the subject,
    at least one processor programmed to:
    detect a marker in said video data, wherein said marker is attachable to a body of the subject, wherein the marker comprises a machine readable graphical pattern, and wherein the graphical pattern comprises encoded data including information about the subject, and
    determine said encoded data from said graphical pattern, and
    extract in dependence of the encoded data a vital sign parameter related to the vital sign of the subject from said video data;
    determine a vital sign of the subject from said vital sign parameter; and
    output the vital sign.

11. A method for determining a vital sign of a subject, comprising:
    attaching a marker to a body of the subject, wherein the marker comprises a machine readable graphical pattern and wherein the graphical pattern comprises encoded data including information about the subject,
    with at least one camera, obtaining video data of the subject,
    with at least one processor, detecting said marker in said video data and determining said encoded data from said graphical pattern,
    with the at least one processor, extracting in dependence of the encoded data a vital sign parameter of the subject from said video data,
    with the at least one processor, determining a vital sign of the subject from said vital sign parameter; and
    with the at least one processor, outputting the vital sign.

12. A non-transitory computer-readable medium storing instructions for causing a computer to carry out the method as claimed in claim 11 when said computer program is carried out on the computer.

13. The method according to claim 11, further including:
    with a first camera, obtaining first video data of the subject;
    with a second camera, obtaining second video data of the subject, and
    with the at least one processor, detecting said marker in said first and second video data.

14. The system according to claim 13, wherein said vital sign parameter is at least one of:
- a respiratory movement of the subject and wherein said vital sign is a respiratory rate of the subject; and
- a temporal variation of a skin color of the subject and wherein said vital sign is a heart rate of the subject and/or a concentration of a substance in blood and/or tissue.

15. The system according to claim 10, wherein the marker further comprises an orientation indicator separate from the graphical pattern for indicating the orientation of the marker.

16. The system according to claim 10, wherein the at least one processor is calibrated using a location and/or orientation of the marker.

17. The system according to claim 10, wherein the at least one camera includes:
- a first camera configured to obtain first video data of the subject;
- a second camera for obtaining second video data of the subject, and
- wherein the at least one processor is programmed to detect said marker in said first and second video data.

18. The system according to claim 17,
- wherein the first camera comprises a filter for selectively transmitting light at a first wavelength, and
- wherein the second camera comprises a second filter for selectively transmitting light at a second wavelength.

19. The system according to claim 1, wherein the encoded data includes a plurality of structural elements configured for a machine-readable determination of the at least one of the orientation and location of the graphical pattern of the marker.

20. The system according to claim 19, wherein the at least one processor is further programmed to:
- determine at least one of a location and orientation of the plurality of structural elements of the graphical pattern of the marker; and
- determine a vital sign parameter related to the vital sign of the subject from the determined at least one of a location and orientation of the plurality of structural elements of the graphical pattern of the marker.

* * * * *